(12) United States Patent
Cardenas-Valencia et al.

(10) Patent No.: US 7,024,060 B2
(45) Date of Patent: Apr. 4, 2006

(54) METHOD AND APPARATUS FOR CONTINUOUS MEASUREMENT OF THE REFRACTIVE INDEX OF FLUID

(75) Inventors: Andres M. Cardenas-Valencia, St. Petersburg, FL (US); Eric Toby Steimle, St. Petersburg, FL (US); Robert H. Byrne, St. Petersburg, FL (US); Melynda Calves, Riverview, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/307,623

(22) Filed: Dec. 2, 2002

(65) Prior Publication Data

US 2004/0105607 A1    Jun. 3, 2004

(51) Int. Cl.
    *G02B 6/00* (2006.01)
(52) U.S. Cl. ...................................................... 385/12
(58) Field of Classification Search ................. 385/12
    See application file for complete search history.

(56) References Cited

U.S. PATENT DOCUMENTS

| | | | |
|---|---|---|---|
| 3,999,857 A * | 12/1976 | David et al. ................. | 356/133 |
| 4,712,096 A | 12/1987 | Cholin et al. | |
| 4,827,121 A | 5/1989 | Vidrine, Jr. et al. | |
| 5,201,220 A * | 4/1993 | Mullins et al. .......... | 73/152.42 |
| 5,325,170 A * | 6/1994 | Bornhop .................... | 356/128 |
| 5,367,583 A | 11/1994 | Sirkis | |
| 5,493,113 A | 2/1996 | Dunphy et al. | |
| 5,585,634 A | 12/1996 | Stevenson et al. | |
| 5,641,956 A | 6/1997 | Vengsarkar et al. | |
| 5,646,400 A | 7/1997 | Perez et al. | |
| 5,769,540 A | 6/1998 | Schietinger et al. | |
| 6,012,337 A | 1/2000 | Hodge | |
| 6,035,082 A | 3/2000 | Murphy et al. | |
| 6,144,026 A | 11/2000 | Udd et al. | |
| 6,181,841 B1 | 1/2001 | Hodge | |
| 6,204,920 B1 | 3/2001 | Ellerbrock et al. | |
| 6,239,876 B1 | 5/2001 | Brandenberg | |
| 6,360,031 B1 | 3/2002 | Harrah | |
| 6,366,722 B1 | 4/2002 | Murphy et al. | |
| 6,399,939 B1 | 6/2002 | Sundaresan et al. | |
| 6,426,045 B1 * | 7/2002 | Jeng et al. ................ | 422/82.05 |

FOREIGN PATENT DOCUMENTS

| JP | 63041804 A | * | 2/1988 |
|---|---|---|---|
| JP | 63044609 A | * | 2/1988 |

OTHER PUBLICATIONS

Turan et al, Fiber Optic Refractometer for Liquid Index of Refraction Measurements, Sep. 2001, TELSIKS 2001, pp. 489-492.*

* cited by examiner

*Primary Examiner*—Juliana Kang
(74) *Attorney, Agent, or Firm*—Michael M. McGaw; Smith & Hopen, P.A.

(57) ABSTRACT

An apparatus and method are herein disclosed which utilize a ratio based on a varied angle of incidence of light on an optical fiber analysis system. By calculating the ration of light incident on the sample element, variations in the system parameters which can provide deleterious effects are obviated.

10 Claims, 4 Drawing Sheets

Refractive indices of air and two glasses, suprasil and barium flint.

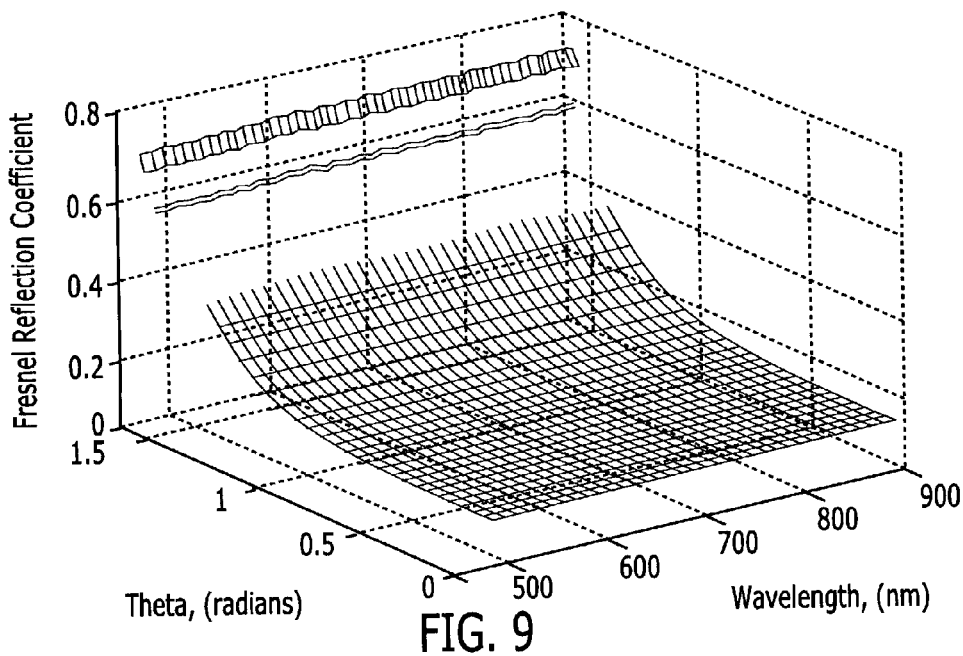
FIG. 9
| Material | Refractive index (at 600 nm) | Acceptance angle, radians (degrees) | |
|---|---|---|---|
| | | Suprasil | Barium flint glass |
| Water | 1.3327 | 0.6325 (36.24) | 1.0522 (60.29) |
| Acetone | 1.3588 | 0.5571 (31.92) | 0.9742 (55.82) |
| Ethanol | 1.3613 | 0.5493 (31.47) | 0.9668 (55.39) |
| Cyclohexane | 1.4260 | 0.3087 (17.69) | 0.7826 (44.84) |
| Glycerol | 1.4718 | - | 0.6482 (37.14) |
| Ethyl salicylate | 1.5194 | - | 0.4909 (28.13) |
| Methyl salicylate | 1.5333 | - | 0.4381 (25.1) |
FIG. 10
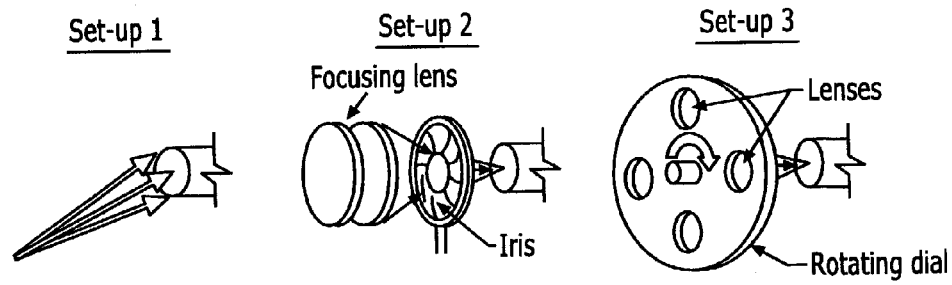
FIG. 11

METHOD AND APPARATUS FOR CONTINUOUS MEASUREMENT OF THE REFRACTIVE INDEX OF FLUID

BACKGROUND OF THE INVENTION

This invention relates to the area of material analysis and the measurement of parameters which identify properties of certain materials. More specifically, this invention is directed toward a system for in situ measurement of the changes of the refractive index of a material which can be used to monitor the changes of that material which is subjected to environmental stresses. In addition the instant invention also relates to the area of chemical analysis and the equipment necessary to perform many types of chemical analyses for a wide variety of applications.

FIELD OF THE INVENTION

Waveguide optical sensors in which a stripped-cladding or exposed core section becomes in contact with the measured fluid have found many applications. The most measured parameter in these sensors is the real term of the refractive index, and in some cases a reflectance property of some intermediate structure in the system itself. One of the obstacles in the current systems is a more accurate calibration method which uses the same detection circuitry to simplify both the size and the cost of the instrumentation. To this end, the development of a self-calibrating system affords the best solution to both instrumental design simplification as well as overcoming undesired aspects found in conventional systems.

With the use of a self-calibration procedure, development of continuous monitoring sensors is possible. Not only does the instant invention address the self-calibration issue, but it has been found that the instant procedure is applicable to both $n_{core} > n_{measured\ fluid}$ and $n_{core} < n_{measured\ fluid}$ systems. In addition, the system of the instant invention may be applied to solid state systems such as, but not limited to, glass materials.

The importance of fiber optic sensors is well known and the number of applications has steadily grown for various decades. They continue to be an active area of research due to the fact that they are generally of low cost, with potential for good performance in a number of diverse applications. Waveguides can be fabricated with different materials that can withstand harsh environments. Their flexibility allows for the sensors to be located in otherwise inaccessible areas. In addition, the light interaction is instantaneous and coupled with the development of rapid sensors, system designs allow for quick and continuous monitoring.

Various systems using corrosion monitors are also known in the art, many of these involving in situ sensors for evaluation of the impact of the use environment. Common to all these systems is the measurement of the change in the optical characteristics of the surface being tested with various detection systems used to analyze the data produced by the optical system. Because most of these analysis systems require complex electronics or algorithms, there is a need to simplify the analytical portion of the system to provide accurate yet simplified analyses to be made.

One such system is disclosed in Cholin et al, U.S. Pat. No. 4,712,096. Here conditions are measured by change in the amount of radiant power between the source and the receiving device at the end of the cladded material. Because the intensity of the emitted light by the source is used to calculate the change ratio, this system is reliant upon a constant source and any fluctuations in the intensity can cause a change in the end ratio, which can lead to false results.

Various systems incorporating Bragg gratings are also known in the art. One of these is disclosed in U.S. Pat. No. 5,493,113 to Dunphy et al. In this type of detection a modulating zone is formed in the core material which acts as a filter to select certain wavelengths for transmission. Because of the nature of the structure of this part of the core material, the complexity of the system makes it more expensive to produce as well as still dependent on the reliability of the source since no compensation is made for variations in the performance characteristics of the source as a function of the changes sensed by the detection system.

Other Bragg systems are disclosed in Murphy et al, U.S. Pat. Nos. 6,035,082 and 6,366,722, Perez et al, U.S. Pat. No. 5,646,400, Udd et al, U.S. Pat. No. 6,144,026, Ellerbrock et al, U.S. Pat. No. 6,204,920 and Vengsarkar et al, U.S. Pat. No. 5,641,956. Even though each of these system addresses solutions to the problems posed by the Bragg structure systems, it is still quite apparent that deficiencies that these systems pose coupled with the high cost of the sensor itself are not overcome by changes or refinements made to the grating type of system.

Brandenberg in U.S. Pat. No. 6,239,876 describes a dual pathway system in which a reference beam is compared to the intensity of a measurement beam. This system takes into consideration the fluctuations in the light source but because a dual detection system is necessary, it becomes a costly instrument to produce as well as a bulky instrument. In addition, any defects in either of the detector portions can cause false results to be obtained.

Another similar system is disclosed in Schietinger et al, U.S. Pat. No. 5,769,540. Again the dual path reference system is used and the additional feature of a plurality of reflectance readings is added to the experimental protocol. These readings may be made at various angles with respect to the surface of the sample to be analyzed but changes are always a function of the difference with light path measurement and not with the angular readings themselves.

Harrah, U.S. Pat. No. 6,360,031, describes another method of measuring the differences in the optical properties in a similar system by having dual clad reflectance. Here two measurements are taken, but these are of differences in the layers and not in any angles with respect to one layer itself.

Sundaresan et al, U.S. Pat. No. 6,399,939 address the issue of corrosion monitoring by use of a sensor array system which includes optical sensors. Here an array of differing types of sensors transits various types of information but there is no discussion of any angle modulation to enhance sensor performance.

Another type of array system is described in U.S. Pat. No. 6,181,841 to Hodge. Here the array is attached to structure via a harness arrangement and the optical portions are monitored as a part of the whole system which includes a reflective grid structure that changes with corrosion and movement of the superstructure. Again, the sensors give only single readings which are valued over periods of time. Hodge, U.S. Pat. No. 6,012,337 is a related disclosure and describes the same type of system.

Other optical measurement systems are known as the Fabry-Perot type of system. One such system is described in Sirkis, U.S. Pat. No. 5,367,583. Here again the changes in optical properties are measured with respect to a single angular reflectance which changes as a function of wear or strain. This type of system also does not use a plurality of angular measurements as a comparison for equating changes in the system.

SUMMARY OF THE INVENTION

It is therefore an object of the invention to provide a system for measurement of refractive properties of a system.

It is a further object of the invention to provide a system for measurement of the refractive properties of a system that compensates for fluctuations in source intensity and is capable of being incorporated into systems that utilize low cost source and detection equipment.

It is another object of the invention to provide a system for measurement of the refractive properties of a system that provides a ratio measurement that is symptomatic of changes within that system.

Still additional objects will become apparent as the instant invention is further described.

BRIEF DESCRIPTION OF THE DRAWINGS

FIG. 9 shows the Fresnel reflection losses calculated as a function of angle and wavelength barium flint glass and air.

FIG. 10 is a table of the refractive indices at 600 nm along with the acceptance angle calculations for fused silica and barium flint glasses.

FIG. 11 is a depiction of three proposed angle modulation devices.

DESCRIPTION OF THE PREFERRED EMBODIMENT OF THE INVENTION

Figure 1:
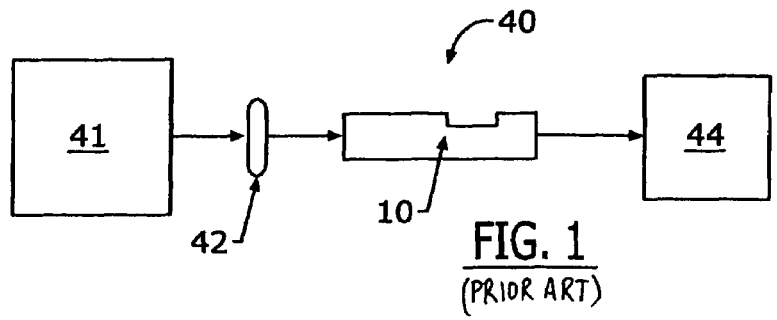
FIG. 1 is a schematic showing a typical prior art system incorporating a waveguide sensor.

In intrinsic sensors, the waveguide, which is normally of generally cylindrical shape, contributes to the measured change, by virtue of a modification of its light transmission characteristics as it interacts with the sample. This common approach couples the use of a cylindrical optical fiber with a section of non-cladding which serves as the sensing transducer that is exposed to the measured fluid and is shown in FIG. 1. Some of the names for these devices include evanescent and total loss absorption spectroscopy fiber optic sensors. Of these intrinsic type of sensors, the oldest and most common are the refractive index detectors.

Referring now more specifically to FIG. 1, the optical sensor system 40 comprises source 41, optically connected to focusing element 42, which in turn is optically connected to the optical fiber element 10, which conveys the light finally to the detector section 44. In most of the prior art devices, the source 41 is a laser type of source, although other types have been used, the laser being preferred because of its ability to supply consistent wavelengths, in spite of the cost of that feature.

Figure 2:
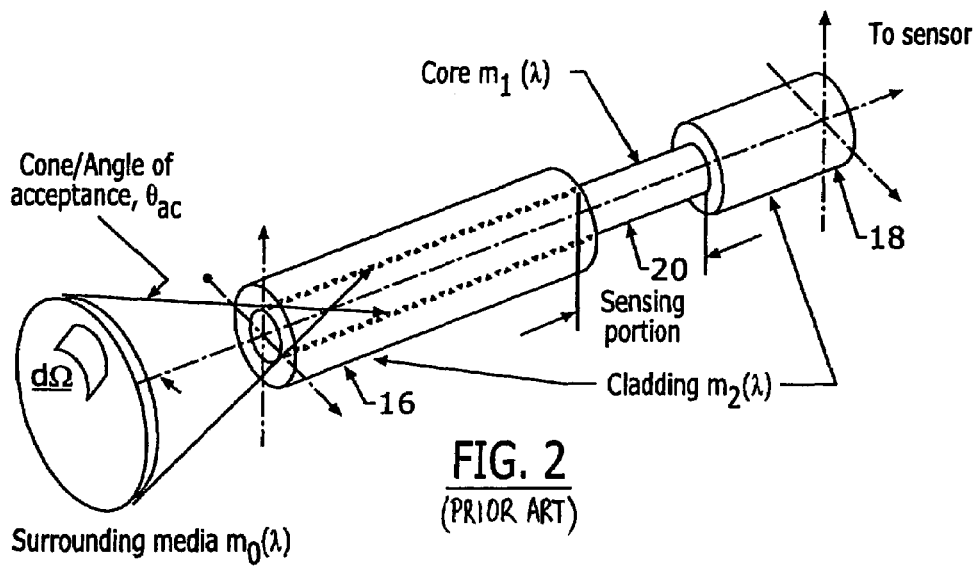
FIG. 2 is a more detained showing of the optical fiber section of FIG. 1.

The optical fiber element 10 is shown in more detail in FIG. 2. In this depiction, the light path travels from the source 41 (not shown) through the focusing element 42 to the optical fiber element 10. This optical fiber element 10 contains both cladded portions 16 and 18 connected to the sensing region 20. This sensing region is then exposed to the environment to be sensed, such as a fluid or a solid state used in corrosion studies. As shown, this sensing region 20 may be a portion of the optical fiber element 10, or may comprise the entire length of the element. The change in the optical properties determines the parameter to be ascertained and in the past this included: gas analysis, chemistry, pH, corrosion, biomaterial assay and various material science applications.

Figure 3:
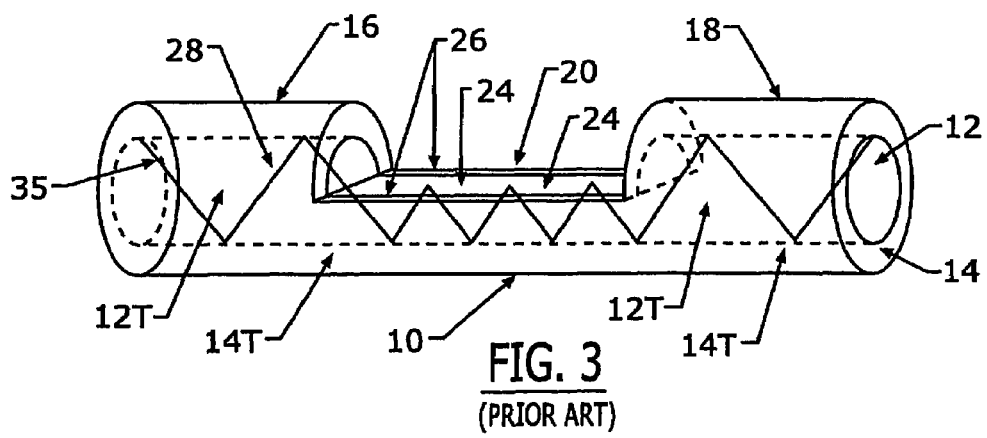
FIG. 3 shows the light path of the typical sensor of the prior art.

The light pathway of the prior art systems as exemplified by Stevenson et al, U.S. Pat. No. 5,585,634 are shown in FIG. 3. In this optical fiber element 10, the fiber member comprises a core portion 12 surrounded by cladding 14 which make up the transmission portions labeled with a T. The sensor portion 20 shows the stripped portions of the cladding as 26 and the inner core portion as 24. Clearly shown is the light path 35 which travels the entire extent of the optical fiber element 10 and interacts with the environment to be tested in the sensor portion 20. Note that only a single beam is used in this prior art example.

In this type of system, the refractive index, n, is ascertained by measuring the transmitted light intensity or by the variation in the angle of the input light. Because of the need for the illumination intensity to be fixed for calculation purposes, laser light has been customarily used due to the fact that other sources such as white light are hard to keep as a non-variable. Thus, absolute methods to quantify light irradiance require precise and costly instrumentation. In many of the prior art devices the signal is normalized at a certain value of the refractive index that represents the maximum light out-put. This is generally accepted as an approach in most light sensors and typically the signal measured when in the sampling mode is compared to a known reference such as a calibration. The calibration, or normalization however is troublesome and is not constant over time, requiring further calibration steps to be performed.

Figure 4:
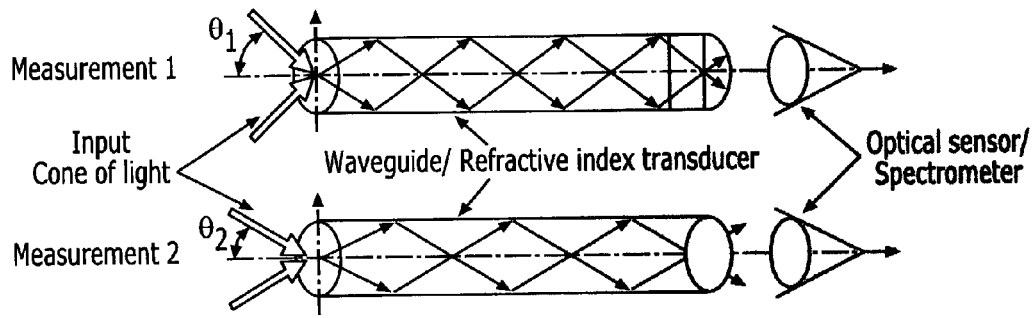
FIG. 4 is a schematic of the refractive index generating system of the instant invention.

The photo-refractometer of the instant invention uses a second measurement as shown in FIG. 4. As depicted, two measurements are taken, but in practice any number of measurements at differing angles may made, as long as there are a plurality of measurements at a corresponding plurality of angles. In the instant system, one measurement is taken with a specified angular input, which is quickly followed by a measurement at a second input angle. The first independent measurement is then divided by the other.

The ratio so obtained is the value that is related to the measured refractive index. By referencing the signal, different effects are taken into account: variation in power and light luminance; Fresnel losses; the absorption attenuation throughout the length of the fiber; and any other light intensity variations. The angular ratio can be defined as:

$$\text{Ratio} = \frac{A2\pi \int_0^{\theta_1} F(\theta')(1 - R_l(\theta'))^2 \rho(\lambda)^{N(\theta')} e^{\frac{Kl}{\cos(\theta')}} \sin\theta d\theta}{A2\pi \int_0^{\theta_2} F(\theta')(1 - R_l(\theta'))^2 \rho(\lambda)^{N(\theta')} e^{\frac{Kl}{\cos(\theta')}} \sin\theta d\theta}$$

Figure 5:
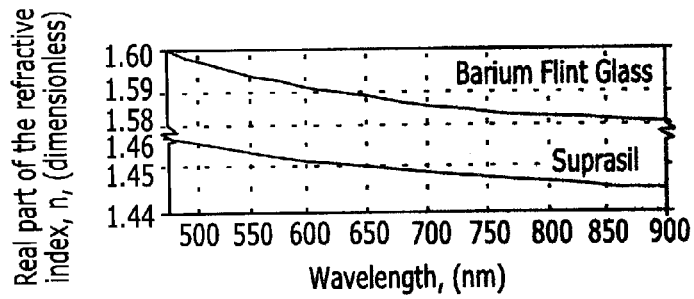
FIG. 5 shows the plot of the refractive indices of two glasses with respect to frequency.

In order to simplify this equation for practical purposes, several aspects were studied to determine those variables which had to be adjusted as being contributors to the integrand terms. In order to obtain realistic estimates, the calculations were performed in the visible range using known refractive indices, these being: air; fused silica and barium flint glass. A plot of the glasses refractive indices as a function of frequency is shown in FIG. 5.

EXAMPLES

Component Analyses

Example 1

Absorption Component

Since the absorption coefficient of most glasses is very small in the visible region of the electromagnetic spectra, the light attenuation can be neglected up to considerable distances, thus it has been neglected in the past in photorefractometric sensors. However, to test this assumption, anyway, the magnitude of the absorption changes due to the angular variation of input rays was investigated. This was accomplished by mathematically representing the absorption as:

$$\text{Absorption} = e^{-KL/\cos(\theta')} = e^{-Kl\sec(\theta')}$$

The term K is multiplied by the secant of the refracted angle in the fiber $\theta'$. Plots of the secant of the refracted angle, $\theta'$, as a function of the illuminating angle, $\theta$ are observed in FIGS. 6 and 7.

Figure 6:
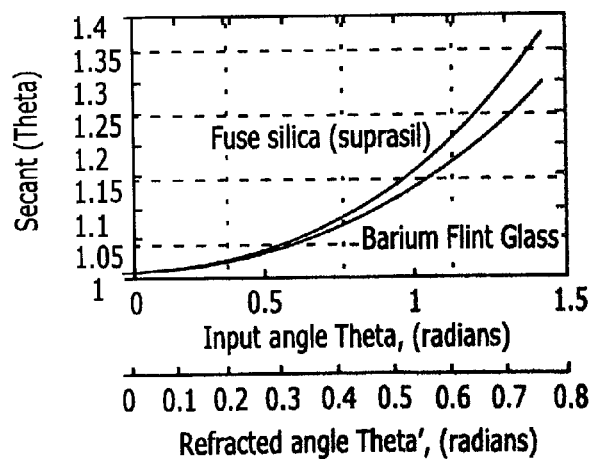
FIG. 6 represents a plot of the secant of a refracted angle as a function of the illuminating angle.
Figure 7:
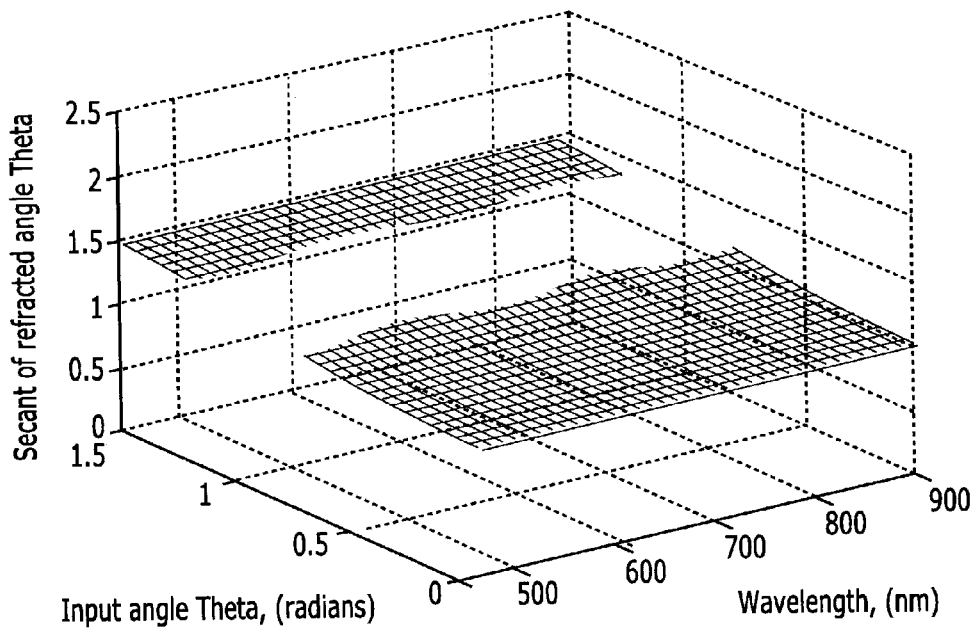
FIG. 7 represents an additional depiction of the material of FIG. 6.

FIG. 6 reveals that the maximum refracted angle, $\theta'$ possible for the two glasses considered is within the order of 0.8 radians. It was observed in FIG. 6 that the value of the secant of an angle is almost constant and has a value of 1 for a wide variety of angles. Thus, it was concluded that there is a negligible angular dependence in the absorption in the cylindrical glass rod.

Fresnel Reflection Losses

As light enters the fiber or dielectric refractive media, from air a certain amount of the amplitude of the electromagnetic waves will be lost as reflection. The Fresnel reflection formulas quantify these losses at the ends of the sensor. The reflection components are given by the equations:

$$R_{lp} = \left( \frac{n_o\cos(\theta) - (n_1^2 - (n_o\sin(\theta))^2)^{1/2}}{n_o\cos(\theta) + (n_1^2 - (n_o\sin(\theta))^2)^{1/2}} \right)^2$$

$$R_{ls} = \left( \frac{-n_1^2\cos(\theta) + (n_1^2 - (n_o\sin(\theta))^2)^{1/2}}{n_1^2\cos(\theta) + (n_1^2 - (n_o\sin(\theta))^2)^{1/2}} \right)^2$$

For un-polarized light the total reflection loss coefficient is given by:

$$R_l = \frac{1}{2}(R_{lp} + R_{ls})$$

Figure 8:
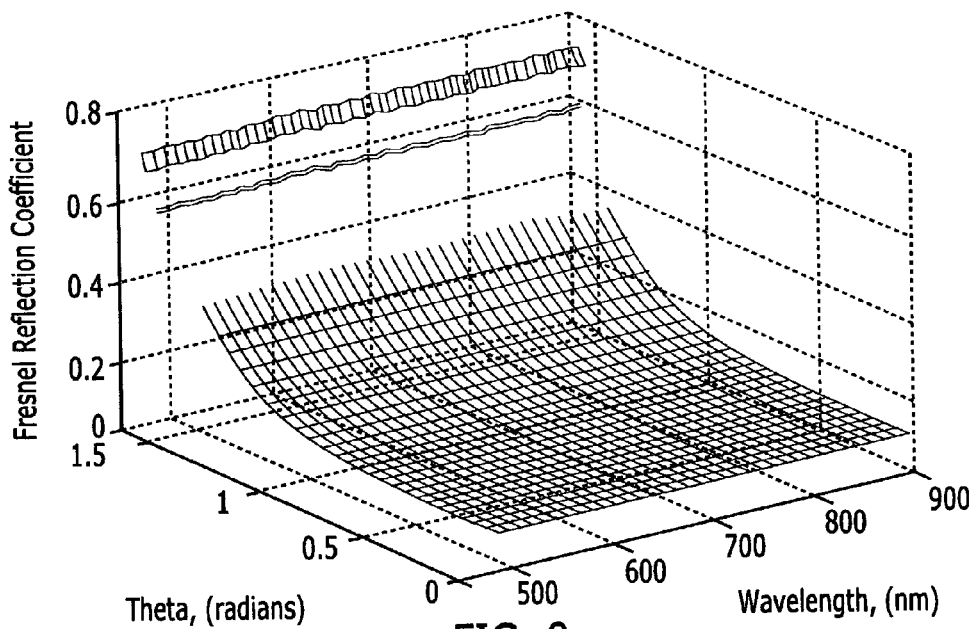
FIG. 8 shows the Fresnel reflection losses calculated as a function of angle and wavelength for fused silica and air.

To appreciate the magnitude of these losses as a function of wavelength, sensors made of fused silica and barium flint glass were considered. These Fresnel values are shown in FIGS. 8 and 9. There it is revealed that the angular dependence is not very pronounced at smaller angles (those up to 1 of input theta). This fact shows that the $R_1$ value is effectively constant for a wide angular range, for the two considered glasses with air as the surrounding medium.

Both the Fresnel reflection losses as well as the secant function of the input angle have shown a very small deviation over the wavelength range considered, so a constant angular dependence is available for a wide variety of input illuminating angles.

Calculation of the Reflectivities

The reflectivity between two dielectric materials can be calculated as the amplitude reflection coefficients given by the Fresnel reflection laws. For the total internal reflection the following equations are used:

$$r_s = -\sin(\theta'-\phi)/\sin(\theta'+\phi)$$

and $$r_p = -\tan(\theta'-\phi)/\tan(\theta'+\phi)$$

Finally, $\rho = R_{s,p}$ is calculated by use of The angles, $\theta$ and $\phi'$, are functions of the optical properties of the material that comprises the waveguide. For the case in which the refractive index of the core is of a smaller magnitude, no total internal reflection occurs.

Simulation Details

Equations a-d define the reflection of a light ray when incident on a dielectric surface. From the above examples, it has been demonstrated that the Fresnel end sensor and absorption losses can be considered as constant over a wide angular input. By use of the ratio equation (a), the resulting constant values due to these effects will be canceled.

Tests of Selected Optical Properties

To show the validity of the usage of the angular ratio as a way to estimate the parameters, several simulations were performed to predict the behavior of the sensor. For this several liquids with known refractive indices in the visible range were chosen. FIG. 10 shows a table of the refractive indices at 600 nm along with the acceptance angle calculations obtained from using the ratio equation (a) for the two glasses mentioned above.

Because the refractive index is a function of the wavelength, the sensing waveguide and sensor may be made to be more sensitive to changes in refractive index by optimizing the angular ratio. In addition, the instant system is capable of using light sources in a variety of wavelengths including visible, infrared and ultraviolet portions of the spectrum.

In addition to the flexibility in the light sources available to one of ordinary skill in the art, a wide variety of detection devices may also be used. These include those which monitor a single wavelength and those which are adapted to detect a plurality of wavelengths either simultaneously, selectively or sequentially. With this system, it is also contemplated that a modular replacement type of component system, having a plurality of replaceable elements is possible.

The apparatus for performing the angular deviations may incorporate any type of focusing device that serves to vary the angle of the light entering the optical fiber element 10. FIG. 11 shows three possible schematics for the angular selection apparatus. These include a source movement means, a focusing lens and iris apparatus and a rotating dial mechanism which is used as a beam splitter in conjunction with holes modulated to vary the angle of the light beam passing therethrough. FIG. 11 is merely representative of a few ways of varying the angles; indeed, other means for achieving the same purpose are considered within the scope of those of ordinary skill in the art. In addition, the apparatus may also include a data processing system to automatically calculate the ratio and the subsequent refractive index. In addition, this data processing system may provide storage of results so that the entire system may be remotely located for monitoring with data retrieval or data conveyance to another monitoring location.

The optical fiber system 10 may be adapted to be a part of any type photometric device by those of ordinary skill in the art. Because the required hardware necessary to implement these changes are contained in an angular deviation means, this change makes the system applicable to a wide variety of operating systems.

Modification and variation can be made to the disclosed embodiments of the instant invention without departing from the scope of the invention as described. Those skilled in the art will appreciate that the applications of the present invention herein are varied, and that the invention is described in the preferred embodiment and the examples. Accordingly, additions and modifications can be made without departing from the principles of the invention. Particularly with respect to the claims it should be understood that changes may be made without departing from the essence of this invention. In this regard it is intended that such changes would still fall within the scope of the present invention. Therefore, this invention is not limited to the particular embodiments disclosed, but is intended to cover modifications within the spirit and scope of the present invention as defined in the appended claims.

What is claimed is:

1. A method for measuring the refractive index of a fluid, comprising the steps of:
    providing a waveguide, wherein the waveguide comprises a cylindrical rod having a first end face and a second end face;
    inputting a first light into the first end face of the waveguide, at a first angle of incidence to the first end face;
    inputting a second light into the first end face of the waveguide, at a second angle of incidence to the first end face, wherein the second angle differs from the first angle;
    detecting, using a single detection device, the first light and second light upon exit from the second end face, wherein the second light is detected subsequent to the first light being detected; and
    comparing, using the first and second angles, a measurement of the first light taken at the second end face to a measurement of the second light taken at the second end face, wherein the step of comparing automatically compensates for fluctuations in intensity of the first light and second light without the use of a reference measurement received external to the single detection device.

2. The method of claim 1, wherein the steps of inputting are implemented by at least one optical lens.

3. The method of claim 1, wherein the step of comparing comprises, at least in part, taking a ratio of the measurement of the first light and second light taken at the second end face.

4. The method of claim 3, further comprising the step of storing the ratio in a database.

5. The method of claim 1, wherein the inputting and comparing steps are repeated consecutively over a period of time.

6. The method of claim 1, wherein the step of providing a waveguide comprises providing a waveguide comprising a sensing portion.

7. The method of claim 1, wherein the step of inputting a first light comprises the step of inputting a first light into the first end face of the waveguide, wherein said first light forms a conical shape.

8. The method of claim 7, wherein the detector forwards the measurements of the first and second light taken at the second end face of waveguide to a computer program product.

9. The method of claim 8, wherein the computer program product implements the comparison step.

10. The method of claim 1, wherein the step of comparing is used to effect corrosion monitoring.

\* \* \* \* \*